United States Patent [19]

Kuhla

[11] 4,129,567
[45] Dec. 12, 1978

[54] QUATERNARY SALTS AS HYPOGLYCEMIC AGENTS

[75] Inventor: Donald E. Kuhla, Gales Ferry, Conn.

[73] Assignee: Pfizer Inc., New York, N.Y.

[21] Appl. No.: 822,738

[22] Filed: Aug. 8, 1977

Related U.S. Application Data

[60] Division of Ser. No. 712,204, Aug. 6, 1976, Pat. No. 4,044,015, which is a continuation-in-part of Ser. No. 609,914, Sep. 3, 1975, abandoned.

[51] Int. Cl.$^2$ .......................................... C07D 487/00
[52] U.S. Cl. .................................................. 546/121
[58] Field of Search ................................. 260/296 H

[56] References Cited

U.S. PATENT DOCUMENTS 4,044,015  8/1977  Kuhla ........................... 260/294.8C

OTHER PUBLICATIONS

El'tsov et al., Zhur. Org. Khim, vol. 8, (English version), pp. 419–423, (1972), (translated from Zhur. Org. Khim., vol. 8, pp. 418–423).

El'tsov et al., Zhur Org. Khim., vol. 8, (English version), pp. 2484–2488, (1972), (translated from original, pp. 2437–2442).

Lizogub et al., Zhur Obsch. Khim., vol. 43, (English version), pp. 2280 to 2284, (translated from original Russian Version, pp. 2291–2296), 1973.

Bradsher et al., J. H. Heterocyclic Chemistry, vol. 2, pp. 331–334, (1965).

Habermalz et al., Chem. Ber. vol. 108, pp. 984–985, (1975).

Primary Examiner—John D. Randolph
Attorney, Agent, or Firm—Connolly and Hutz

[57] ABSTRACT

The synthesis of imidazo[1,2-a]pyridinium, imidazo[1,5-a]pyridinium, pyrrolo[1,2-a]pyrazinium, pyrazolo[1,5-a]pyridinium, imidazo[2,1-a]isoquinolinium and imidazo[5,1-a]isoquinolinium quaternary salts and their use as hypoglycemic agents.

4 Claims, No Drawings

QUATERNARY SALTS AS HYPOGLYCEMIC AGENTS

CROSS-REFERENCE TO RELATED APPLICATIONS

This application is a division of application Ser. No. 712,204 as filed Aug. 6, 1976, and now U.S. Pat. No. 4,044,015, which in turn is a continuation-in-part of application Ser. No. 609,914, filed Sept. 3, 1975 and now abandoned.

BACKGROUND OF THE INVENTION

This invention relates to fused heterocyclic quaternary salts as hypoglycemic agents, and more particularly to imidazo[1,2-a]pyridinium, imidazo[1,5-a]pyridinium, pyrrolo[1,2-a]pyrazinium, pyrazolo[1,5-a]pyridinium, imidazo[2,1-a]isoquinolinium and imidazo[5,1-a]isoquinolinium quaternary salts as orally-effective blood sugar lowering agents in the treatment of diabetes.

Other than insulin, which is usually administered subcutaneously, the most useful oral medication employed in the treatment of diabetes are the sulfonylureas, many of which are currently being marketed. In addition, biguanides are also employed either alone or in combination with sulfonylureas in the treatment of this disease.

Recently, 1-substituted 3-(2-pyrimidinyl)imidazolium salts have been claimed in Belgium Pat. No. 743,510 and German Patent Application 1,964,282, to be active as hypoglycemic agents. Japanese Patent Application 7305899 reports the synthesis of pyridinium-pyrazine and their use as lowerers of blood sugar and free fatty acid levels. Wiegand, et. al., *J. Med. Chem.*, 15, 1326 (1972), review and report on the hypoglycemic activity of a number of azolylpyridinium salts, while U.S. Pat. No. 3,860,718 teaches the use of imidazo[2,1-b]thiazolium salts as blood sugar lowering agents.

2,3,9-Trimethylbenzimidazo[2,1-b]thiazolium iodide has been prepared by de Stevens, et. al., *J. Am. Chem. Soc.*, 79 5710 (1957), imidazo[2,1-b]thiazolium by Kondo, et. al., *J. Pharm. Soc., Japan,* 57, 1050 (1937) (C.A. 32, 3398 (1938) and Kickhöfen, et. al., *Chem. Ber.,* 88 1109 (1955) (C.A. 50, 13911 [1956]), and imidazo[1,3-a]quinolinium salts by Habermalz, et. al., *Chem. Ber.,* 108, 984 (1975).

Dissertation Abstracts 68-11,711 reports the synthesis of imidazo[1,5-a]pyridine methiodide, while Bradsher, et. al., *J. Heterocyclic Chem.,* 2, 331 (1965), reports the preparation of 1,2,3-trimethylimidazo[1,2-a]pyridinium bromide, 1-methyl-2-phenylimidazo[1,2-a]pyridinium bromide, 1-phenyl-2-methylimidazo[1,2-a]pyridinium bromide, 1-phenylimidazo[1,2-a]pyridinium perchlorate, 1-methylimidazo[1,2-a]pyridinium perchlorate, 1-benzyl-2-phenylimidazo[1,2-a]pyridinium bromide and 1-benzyl-2-methylimidazo[1,2-a]pyridinium bromide.

SUMMARY OF THE INVENTION

It has now been discovered that quaternary salts of imidazo[1,2-a]pyridine, imidazo[1,5-a]pyridine, pyrrolo[1,2-a]pyrazine, pyrazolo[1,5-a]pyridine, imidazo[2,1-a]isoquinoline and imidazo[5,1-a]isoquinoline are orally effective hypoglycemic agents useful in the reduction of blood sugar levels of diabetics.

The first preferred group of compounds are those of the formula:

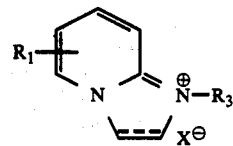

where $R_1$ is hydrogen, chloro, methoxy or benzyloxy; $R_3$ is benzyl, α-naphthylmethyl, β-naphthylmethyl, β-phenethyl or benzyl substituted by chloro, fluoro, dichloro, trifluoromethyl, cyano, methylsulfonyl, dimethylsulfamoyl, carbethoxy, phenyl or methoxy; and X is a pharmaceutically acceptable anion.

The broken line shown in the above structure I represents an optional bond such that the present invention is meant to embrace both the 2,3-dihydro- and dehydro-forms of the imidazo[1,2-a]pyridinium compounds.

Especially preferred within this first group of compounds are those of formula I wherein $R_1$ is hydrogen and $R_3$ is benzyl or substituted benzyl.

The second group of compounds within the scope of the invention are those of the formula:

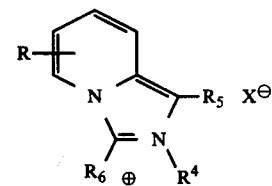

where R is hydrogen or the carbon and hydrogen atoms completing a fused 6,7-benzo moiety; $R_4$ is alkyl having one to three carbon atoms, benzyl or substituted benzyl wherein the substituent is chloro or dichloro; $R_5$ and $R_6$ are each phenyl or hydrogen, provided that when $R_5$ and $R_6$ are both hydrogen, $R_4$ is benzyl or substituted benzyl wherein said substituent is chloro or dichloro; and X is a pharmaceutically acceptable anion. The compound wherein $R_5$ and $R_6$ are both hydrogen, $R_4$ is methyl, R is hydrogen and X is iodide, which is reported of unspecified activity in Dissertation Abstracts 68-11,711, is devoid of any significant hypoglycemic activity.

Especially preferred within this group are compounds wherein R, $R_5$ and $R_6$ are hydrogen. A second especially preferred group are those wherein $R_4$ is methyl and $R_5$ is phenyl. A third especially preferred group of hypoglycemic compounds are those wherein $R_4$ is methyl and $R_6$ is phenyl. A final group of especially preferred compounds are those wherein R is the carbon and hydrogen atoms completing a fused 6,7-benzo moiety and $R_5$ and $R_6$ are each hydrogen.

The third preferred group of compounds within the scope of the instant invention are those of the formulae:

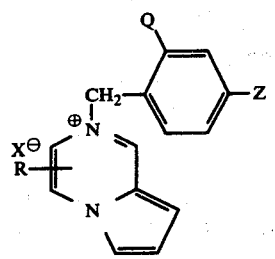

III

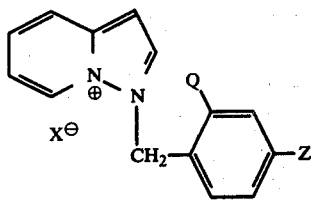

IV

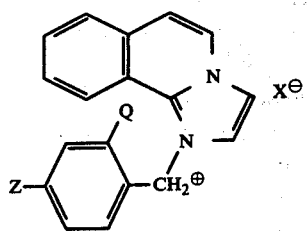

V

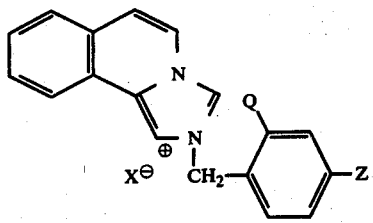

VI where R is hydrogen or the carbon and hydrogen atoms completing a fused 3,4-benzo moiety; Q and Z are each hydrogen or chlorine; and X is a pharmaceutically acceptable anion.

A fourth preferred group of compounds within the scope of the invention are hypoglycemic agents of the formula:

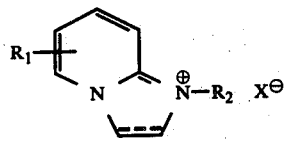

where $R_1$ is hydrogen, chlorine, methoxy or benzyloxy; $R_2$ is furfuryl or 8-quinolylmethyl; and X is a pharmaceutically acceptable anion.

A fifth preferred group of compounds within the purview of the present invention are congeners of the formula:

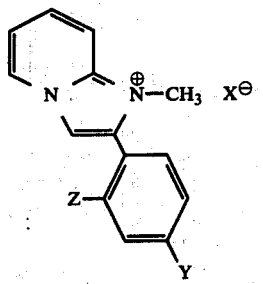

where Y is chlorine, bromine or methoxy; Z is hydrogen or chlorine and X is a pharmaceutically acceptable anion.

In all the aforementioned preferred groups of blood sugar lowering agents, it is preferred that X is chloro, bromo, iodo or sulfate.

Also useful as antidiabetic agents and considered within the scope of the present invention are the known compounds, 1-benzyl-2-phenylimidazo[1,2-a]pyridinium and 1-methyl-2-phenylimidazo[1,2-a]pyridinium salts wherein the anion of said salts are pharmaceutically acceptable ones.

DETAILED DESCRIPTION OF THE INVENTION

The hypoglycemic agents of the present invention are synthesized by the reaction of a suitable halide with the appropriate heterocyclic ring system, depicted as follows:

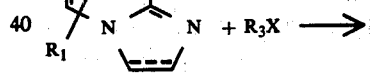

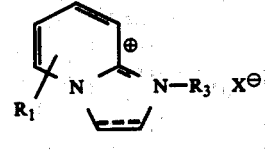

I

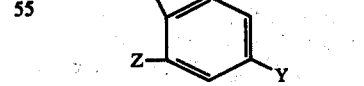

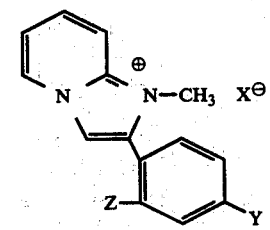

II

-continued

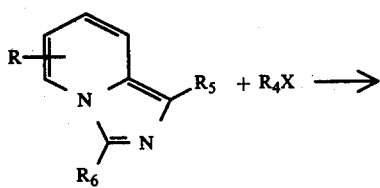

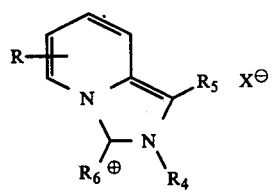

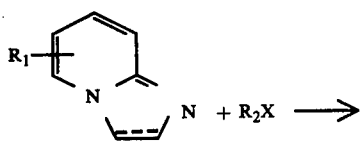

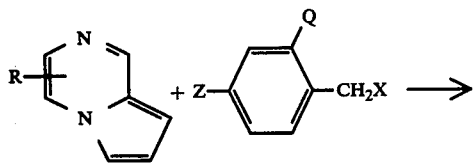

III

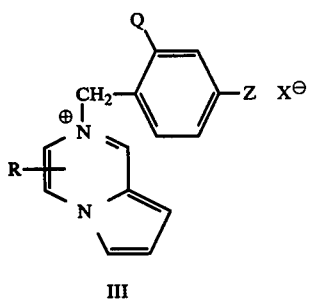

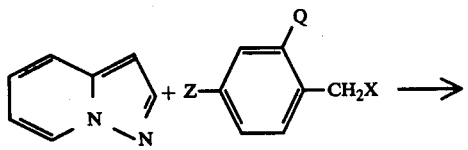

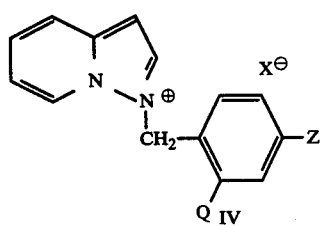

Q IV

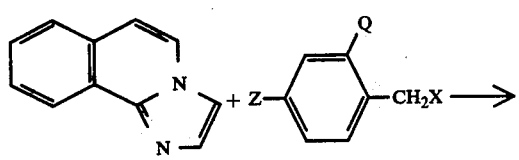

-continued

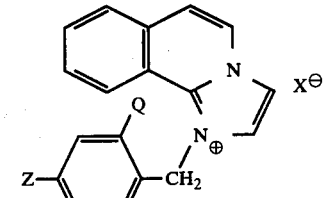

V (structures continue)

VI wherein R, $R_2$, $R_1$, $R_3$, $R_4$, $R_5$, $R_6$, Q, Y, Z and X are as previously described.

Transformation of the above-mentioned heterocyclic compounds to quaternary salts is effected by reacting with a halide where X is preferably chloro, bromo or iodo. Said reaction can be conducted between equimolar amounts of the two reagents either neat or in the presence of a suitable reaction-inert solvent. When conducted neat a large excess of the halide can be employed, acting under these conditions as both a reactant and solvent.

By a reaction-inert solvent is meant one which does not react to any appreciable degree with the product or reactants under the conditions of said reaction. Solvents suitable for the solublizing of the reactants leading to the quaternary compounds can be of a varied nature, and can include (lower)alkanols, (lower)alkylnitriles, di(lower)alkyl ketones, cyclic- and di(lower)alkyl ethers and liquid aromatic hydrocarbons. The preferred solvent for this reaction is acetonitrile.

Reaction time is not critical, and depends on temperature, concentration and inherent reactivity of the reagents. When steam bath temperatures are employed, completion of the reaction usually requires overnight heating.

The product is isolated by cooling the reaction mixture to induce crystallization, or initial concentration of the reaction mixture followed by cooling and addition of a second solvent to induce crystallization. Further purification of the final product is facilitated by trituration or recrystallization from an appropriate solvent.

As mentioned previously, quaternary salt formation is preferably effected wherein X of the alkylating agent is bromo, chloro, or iodo. Following isolation of these salts the nature of the X variable can be altered by initially treating an aqueous solution of quaternary halide with an equivalent of silver oxide, followed by separation of the precipitated silver halide and treatment of the aqueous solution of the quaternary base with at least an equivalent of an appropriate acid HX.

Alternately, the quaternary base can be obtained by passing a solution of a salt through a basic ion-exchange resin column followed by treatment of the eluate with the same or a different acid.

In the utilization of the chemotherapeutic activity of those compounds of the present invention which form quaternary salts, it is preferred, of course, to use pharmaceutically acceptable salts. Although water-insolubility, toxicity, or lack of crystalline nature may make some particular salt species unsuitable or less desirable for use as such in a given pharmaceutical application, the water insoluble or toxic salts can be converted to the corresponding pharmaceutically acceptable quaternary hydroxide by decomposition of the salt as described above, or alternately they can be converted to any desired pharmaceutically acceptable quaternary salt.

Examples of pharmaceutically acceptable anions other than the halides are nitrate, sulfate, phosphate, alkanoates, lactate, citrate, tartrate, succinate and maleate.

The heterocyclic intermediate leading to the quaternary salts of the present invention are prepared by known procedures or by hereinafter described methods. The halide intermediates are commercial reagents or are synthesized by procedures either taught in chemical literature or familiar to those skilled in the art.

As previously mentioned, the quaternary salts are all readily adapted to therapeutic use as oral hypoglycemic agents in view of their ability to lower blood sugar levels of diabetic subjects. Toward this end, the preferred compounds are 1-benzylimidazo[1,2-a]pyridinium bromide, 1-benzyl-6-chloroimidazo[1,2-a]pyridinium bromide, 1-benzyl-8-benzyloxyimidazo[1,2-a]pyridinium, 1-benzyl-5-methoxyimidazo[1,2-a]pyridinium bromide, 1-benzyl-2,3-dihydroimidazo[1,2-a]pyridinium bromide, 1-benzylimidazo[1,2-a]pyridinium chloride, 1-benzylimidazo[1,2-a]pyridinium sulfate, 1-(2-chlorobenzyl)imidazo[1,2-a]pyridinium chloride, 1-(3-chlorobenzyl)imidazo[1,2-a]pyridinium bromide, 1-(4-chlorobenzyl)imidazo[1,2-a]pyridinium chloride, 1-(2-chlorobenzyl)-2,3-dihydroimidazo[1,2-a]pyridinium chloride, 1-(3-chlorobenzyl)-2,3-dihydroimidazo[1,2-a]pyridinium chloride, 1-(4-chlorobenzyl)-2,3-dihydroimidazo[1,2-a]pyridinium chloride, 1-(4-bromobenzyl)imidazo[1,2-a]pyridinium chloride, 1-(2-fluorobenzyl)imidazo[1,2-a]pyridinium chloride, 1-(4-fluorobenzyl)imidazo[1,2-a]pyridinium bromide, 1-(2-bromobenzyl)imidazo[1,2-a]pyridinium bromide, 1-(8-quinolylmethyl)imidazo[1,2-a]pyridinium bromide, 1-furfurylimidazo[1,2-a]pyridinium chloride, 1-methyl-2-(4-chlorophenyl)imidazo[1,2-a]pyridinium iodide, 1-methyl-2-(4-bromophenyl)imidazo[1,2-a]pyridinium iodide, 1-methyl-2-(4-methoxyphenyl)imidazo[1,2-a]pyridinium iodide, 2-(2-chlorobenzyl)imidazo[1,5-a]pyridinium chloride, 2-benzylimidazo[1,5-a]pyridinium bromide, 1-phenyl-2-methylimidazo[1,5-a]pyridinium iodide, 2-methyl-3-phenylimidazo[1,5-a]pyridinium iodide, 2-benzylimidazo[1,5-a]quinolinium bromide, 2-(2-chlorobenzyl)imidazo[1,5-a]quinolinium chloride, 2-benzylpyrrolo[1,2-a]pyrazinium bromide, 1-benzylpyrazolo[1,5-a]pyridinium bromide, 1-benzyl-1H-imidazo[2,1-a]isoquinolinium bromide, 1-(2-chlorobenzyl)-1H-imidazo[2,1-a]isoquinolinium chloride, 2-benzylimidazo[5,1-a]isoquinolinium bromide and 2-(2-chlorobenzyl)imidazo[5,1-a]isoquinolinium chloride.

The quaternary salts, which are useful hypoglycemic agents in mammals, can be administered either as individual therapeutic agents or as mixtures of therapeutic agents. They can be administered alone, but are generally administered with a pharmaceutical carrier selected on the basis of the chosen route of administration and standard pharmaceutical practice. For example, they may be combined with various pharmaceutically acceptable carriers in the form of tablets, capsules, lozenges, troches, hard candies, powders, aqueous suspensions or solutions, injectable solutions, elixirs, syrups and the like. Such carriers include solid diluents or filters, sterile aqueous media and various nontoxic organic solvents. Moreover, the oral pharmaceutical compositions of this invention may be suitably sweetened and flavored by means of various agents of the type commonly used for this purpose.

The particular carrier selected and the proportion of active ingredient to carrier are influenced by the solubility and chemical nature of the therapeutic compounds, the chosen route of administration and the needs of the standard pharmaceutical practice. For example, where those compounds are administered orally in tablet form, excipients such as lactose, sodium citrate, calcium carbonate and dicalcium phosphate may be used. Various disintegrants such as starch, alginic acids, and certain complex silicates, together with lubricating agents such as magnesium stearate, sodium lauryl sulphate and talc, may also be used in producing tablets for the oral administration of these compounds. For oral administration in capsule form, high molecular weight polyethylene glycols are among the preferred materials for use as pharmaceutically acceptable carriers. Where aqueous suspensions are to be used for oral administration, the compounds of this invention may be combined with emulsifying or suspending agents. Diluents such as ethanol, propylene glycol, glycerine and their combinations may be employed as well as other materials.

For purposes of parenteral administration, solutions or suspensions of the instant compounds in sesame or peanut oil or in aqueous propylene glycol solutions can be employed, as well as sterile aqueous solutions described hereinafter. These particular solutions are especially suited for intramuscular and subcutaneous injection purposes. The aqueous solutions dissolved in pure distilled water are also useful for intravenous injection purposes provided that their pH is properly adjusted beforehand. Such isolations should also be suitably buffered, if necessary, and the liquid diluent first rendered isotonic with sufficient saline.

It is necessary that the active ingredient form a proportion of the composition such that a suitable dosage form will be obtained. Obviously, several dosage unit forms may be administered at about the same time. Although compositions with less than 0.005 percent by weight of active ingredient might be used in certain instances, it is preferred to use compositions containing not less than 0.005 percent of the active ingredient; otherwise the amount of carrier becomes excessively large. Activity increases with the concentration of the active ingredient. The composition may contain 10, 50, 75, 95, or an even higher percentage by weight of the active ingredient.

Although the use of the present invention is directed toward the treatment of mammals in general, the preferred subject is humans. In determining an efficacious dose for human therapy, results of animal testing are frequently extrapolated and a correlation is assumed between animal test behavior and proposed human dosage. When a commercially employed standard is available, the dose level of the clinical candidate in humans is frequently determined by comparison of its performance with the standard in an animal test. For example, β-phenethylbiguanide is employed as a standard hypoglycemic agent and is administered to humans at the rate of 50 to 150 mg. daily. It is assumed, then, that if compounds of the present invention have activity comparable to β-phenethylbiguanide in the test assay, that similar doses will provide comparable responses in humans.

Obviously, the physician will ultimately determine the dosage which will be most suitable for a particular individual, and it will vary with the age, weight and response of the particular patient as well as with the nature and extent of the symptoms and the pharmacodynamic characteristics of the particular agent to be administered. Generally, small doses will be administered initially, with a gradual increase in the dosage until the optimum level is determined. It will often be found that when the composition is administered orally, larger quantities of the active ingredient will be required to produce the same level as produced by a small quantity administered parenterally.

Having full regard for the foregoing factors, it is considered that an effective daily dosage of the compounds of the present invention in humans of approximately 50 to 600 mg. per day, with a preferred range of about 50 to 400 mg. per day in single or divided dose, or at about 0.07 to 0.6 mg./kg. of body weight will effectively lower blood sugar levels in human diabetic subjects. These values are illustrative, and there may, of course, be individual cases where higher or lower dose ranges are merited.

The following examples are provided solely for the purpose of illustration and are not to be construed as limitations of this invention, many variations of which are possible without departing from the spirit or scope thereof.

EXAMPLE 1

1-Benzylimidazo[1,2-a]pyridinium Bromide

A. imidazo[1,2-a]pyridine

A mixture of 47 g. of 2-aminopyridine, 120 g. of a 45% chloroacetaldehyde solution in water and 50.4 g. of sodium bicarbonate in 400 ml. of anhydrous ethanol and 100 ml. of water is heated to reflux for 3 hrs. The reaction mixture is cooled, treated with 900 ml. of water and extracted with diethyl ether (3 × 700 ml.). The combined extracts are dried over sodium sulfate and concentrated to a brown oil. Distillation gives 18.8 g. of the desired intermediate as a light yellow oil, b.p. 70° C./0.02 mm.

B. 1-benzylimidazo[1,2-a]pyridinium bromide

To 1.77 g. of imidazo[1,2-a]pyridine in 40 ml. of acetonitrile is added 3.42 g. of α-bromotoluene, and the resulting mixture heated to reflux overnight. The resulting solution is cooled, and the precipitated solids filtered. Recrystallization of the crude product from acetonitrile affords the pure product as a white solid, 2.33 g., m.p. 169°–171° C.

Anal. Calc'd for $C_{14}H_{13}N_2Br$: C, 58.2; H, 4.5; N, 9.7. Found: C, 58.1; H, 4.5; N, 9.7.

EXAMPLE 2

Starting with imidazo[1,2-a]pyridine and the appropriate halide, and employing the procedure of Example 1-B, the following quaternary salts are prepared in the indicated % yield:

1-(2,6-Dichlorobenzyl)imidazo[1,2-a]pyridinium chloride (69% yield), m.p. 235°–238° C.

Anal. Calc'd for $C_{14}H_{11}N_2Cl_3$: C, 53.6; H, 3.5; N, 8.9. Found: C, 53.5; H, 3.6; N, 9.1.

1-(2,4-Dichlorobenzyl)imidazo[1,2-a]pyridinium chloride (90% yield), m.p. 207°–213° C.

Anal. Calc'd for $C_{14}H_{11}N_2Cl_3$: C, 53.6; H, 3.5; N, 8.9. Found: C, 53.4; H, 3.6; N, 9.0.

1-(4-Methoxybenzyl)imidazo[1,2-a]pyridinium chloride (85% yield), m.p. 197°–200° C.

Anal. Calc'd for $C_{15}H_{15}ON_2Cl$: C, 65.6; H, 5.5; N, 10.2. Found: C, 65.4; H, 5.5; N, 10.2.

1-(2-Chlorobenzyl)imidazo[1,2-a]pyridinium chloride (62% yield), m.p. 212°–215° C.

Anal. Calc'd for $C_{14}H_{12}N_2Cl_2$: C, 60.2; H, 4.3; N, 10.0. Found: C, 60.2; H, 4.3; N, 10.2.

1-(3-Chlorobenzyl)imidazo[1,2-a]pyridinium bromide (85% yield), m.p. 206°–208.5° C.

Anal. Calc'd for $C_{14}H_{12}N_2BrCl$: C, 51.9; H, 3.7; N, 8.1. Found: C, 52.0; H, 3.7; N, 8.1.

1-(4-Chlorobenzyl)imidazo[1,2-a]pyridinium chloride (81% yield), m.p. 241°–245° C.

Anal. Calc'd for $C_{14}H_{12}N_2Cl_2$: C, 60.2; H4.3; N, 10.0. Found: C, 60.4; N, 4.3; N, 10.1.

1-(4-Cyanobenzyl)imidazo[1,2-a]pyridinium bromide (80% yield), m.p. 216°–218° C.

Anal. Calc'd for $C_{15}H_{12}N_3Br$: C, 57.3; H, 3.9; N, 13.2. Found: C, 57.0; H, 3.8; N, 13.1.

1-(2-Bromobenzyl)imidazo[1,2-a]pyridinium bromide (49% yield), m.p. 229°–232° C.

Anal. Calc'd for $C_{14}H_{12}N_2Br_2$: C, 45.7; H, 3.3; N, 7.6. Found: C, 45.5; H, 3.4; N, 8.7.

1-(4-Bromobenzyl)imidazo[1,2-a]pyridinium chloride (65% yield), m.p. 237°–240° C.

Anal. Calc'd for $C_{14}H_{12}N_2BrCl$: C, 52.0; H, 3.8; N, 8.7. Found: C, 52.1; H, 3.8; N, 8.7.

1-(2-Fluorobenzyl)imidazo[1,2-a]pyridinium chloride (33% yield), m.p. 194°–197° C.

Anal. Calc'd for $C_{14}H_{12}N_2ClF$: C, 64.0; H, 4.6; N, 10.7. Found: C, 63.6; H, 4.6; N, 10.5.

1-(4-Fluorobenzyl)imidazo[1,2-a]pyridinium bromide (33% yield), m.p. 154°–156° C.

Anal. Calc'd for $C_{14}H_{12}N_2BrF$: C, 54.7; H, 3.9; N, 9.1. Found: C, 54.3; H, 4.0; N, 8.9.

1-(3-Trifluoromethylbenzyl)imidazo[1,2-a]pyridinium chloride (43% yield), m.p. 172°–175° C.

Anal. Calc'd for $C_{15}H_{12}N_2F_3Cl.\frac{1}{2}H_2O$: C, 56.4; H, 4.1; N, 8.7. Found: C, 56.0; H, 4.1; N, 8.7.

1-(4-Phenylbenzyl)imidazo[1,2-a]pyridinium bromide (31% yield), m.p. 184°–187° C.

Anal. Calc'd for $C_{20}H_{17}N_2Br$: C, 65.8; H, 4.7; N, 7.6. Found: C, 65.6; H, 4.8; N, 7.6.

1-(4-Methylsulfonylbenzyl)imidazo[1,2-a]pyridinium bromide (76% yield), m.p. 254°–256° C.

Anal. Calc'd for $C_{15}H_{15}O_2N_2SBr$: C, 49.1; H, 4.1; N, 7.6. Found: C, 49.1; H, 4.2; N, 7.7.

1-(4-Sulfamoylbenzyl)imidazo[1,2-a]pyridinium bromide (54% yield), m.p. 252°–255° C.

Anal. Calc'd for $C_{14}H_{14}O_2N_3SBr$: C, 45.7; H, 3.8; N, 11.4. Found: C, 45.3; H, 3.8; N, 11.2.

1-(4-Carbethoxybenzyl)imidazo[1,2-a]pyridinium bromide (44% yield), m.p. 124°–128° C.

Anal. Calc'd for $C_{17}H_{17}O_2N_2Br.\frac{1}{4} H_2O$: C, 55.6; H, 4.9; N, 7.7. Found: C, 55.6; H, 5.1; 1 N, 7.5.

1-(4-Dimethylsulfamoylbenzyl)imidazo[1,2-a]pyridinium bromide (11% yield), m.p. 230°–235° C.

Anal. Calc'd for $C_{16}H_{18}N_3O_2SBr$: C, 48.5; H, 4.6; N, 10.6. Found: C, 48.4; H, 4.7; N, 10.5.

1-(1-Naphthylmethyl)imidazo[1,2-a]pyridinium chloride (62% yield), m.p. 236°–240° C.

Anal. Calc'd for $C_{18}H_{15}N_2Cl$: C, 73.3; H, 5.1; N, 9.5. Found: C, 73.5; H, 5.4; N, 9.3.

1-(2-Naphthylmethyl)imidazo[1,2-a]pyridinium bromide (58% yield), m.p. 172°–176° C.

Anal. Calc'd for $C_{18}H_{15}N_2Br$: C, 63.7; H, 4.5; N, 8.3. Found: C, 63.8; H, 4.7; N, 8.0.

1-(8-quinolylmethyl)imidazo[1,2-a]pyridinium bromide (49% yield), m.p. 228°–230° C.

Anal. Calc'd for $C_{17}H_{14}N_3Br$: C, 60.0; H, 4.2; N, 12.4. Found: C, 59.7; H, 4.2; N, 12.0.

1-(2-Furfuryl)imidazo[1,2-a]pyridinium chloride (21% yield), m.p. 170°–174° C.

Anal. Calc'd for $C_{12}H_{11}ON_2Cl.\frac{1}{4} H_2O$: C, 60.0; H, 5.3; N, 11.7. Found: C, 60.2; H, 4.9; N, 11.7.

1-(2-Phenethyl)imidazo[1,2-a]pyridinium bromide (61% yield), m.p. 170°–172.5° C.

Anal. Calc'd for $C_{15}H_{15}N_2Br$: C, 59.4; H, 5.0; N, 9.3. Found: C, 59.5; H, 5.1; N, 9.1.

EXAMPLE 3

Employing the procedure of Example 1-B, and starting with imidazo[1,2-a]pyridine and the appropriate halide, the following quaternary salts are synthesized:

1-(2,3-dichlorobenzyl)imidazo[1,2-a]pyridinium chloride; 1-(3,5-dichlorobenzyl)imidazo[1,2-a]pyridinium chloride; 1-(3,4-dichlorobenzyl)imidazo[1,2-a]pyridinium bromide; 1-(2-methoxybenzyl)imidazo[1,2-a]pyridinium bromide; 1-(3-methoxybenzyl)imidazo[1,2-a]pyridinium chloride; 1-(3-cyanobenzyl)imidazo[1,2-a]pyridinium iodide; 1-(3-bromobenzyl)imidazo[1,2-a]pyridinium bromide; 1-(3-fluorobenzyl)imidazo[1,2-a]pyridinium bromide; 1-(3-phenylbenzyl)imidazo[1,2-a]pyridinium chloride; 1-(3-sulfamoylbenzyl)imidazo[1,2-apyridinium chloride; 1-(2-methylsulfonylbenzyl)imidazo[1,2-a]pyridinium chloride; 1-(4-trifluoromethylbenzyl)imidazo[1,2-a]pyridinium bromide; and 1-(3-furfuryl)imidazo[1,2-a]pyridinium bromide.

EXAMPLE 4

1-Benzyl-2,3-dihydro-1H-imidazo[1,2-a]pyridinium bromide

A. 2,3-dihydroimidazo[1,2-a]pyridine

A mixture of 72.5 g. of 2-aminopyridine and 67.0 g. of 2-chloroethanol is heated at 110° for 52 hrs. The mixture is cooled to room temperature and is then treated with water and sufficient solid sodium carbonate to give pH 8. Chloroform (200 ml.) is added and the two-phase system heated until a solution results. The aqueous layer is separated, washed again with chloroform 2 × 100 ml.) and subsequently concentrated to dryness. The residue from the aqueous layer is extracted with ethanol. The insolubles are filtered and the ethanol filtrate is allowed to stand at room temperature overnight. The precipitated solids, comprising 30.5 g. of the product, 1-(2-hydroxyethyl)-2-aminopyridinium chloride are filtered. Evaporation of the filtrate to half volume provides an additional 31.4 g. of the desired material, m.p. 146°–149° C.

Fifty grams of the above-mentioned 1-(2-hydroxyethyl)-2-aminopyridinium chloride is converted into 41.0 g., m.p. 178°–180° C., of the desired product as the hydrobromide salt following the procedure of Burton, et al., J. Chem. Soc. (Perkins), (1972), 1940.

Sixteen grams of the hydrobromide salt in 100 ml. of water is treated with 20 ml. of 20% (w/v) aqueous sodium hydroxide solution. The resulting solution is concentrated in vacuo to a low volume and extracted with benzene. The benzene layer is separated, dried over sodium sulfate and concentrated to 8.75 g. of a yellow oil which crystallizes to a low melting solid.

B. 1-benzyl-2,3-dihydro-1H-imidazo[1,2-a]pyridinium bromide

To 2.0 g. of 2,3-dihydroimidazo[1,2-a]pyridine in 40 ml. of dry acetonitrile is added 3.42 g. of α-bromotoluene and the resulting mixture heated to reflux overnight. The solution is cooled to room temperature and treated with 30 ml. of diethyl ether. The precipitated solid is filtered and recrystallized from acetonitrile, 1.64 g., m.p. 143°–145° C.

Anal. Calc'd for $C_{14}H_{15}N_2Br$: C, 57.8; H, 5.2; N, 9.6. Found: C, 57.6; H, 5.0; N, 9.6.

EXAMPLE 5

Starting with 2,3-dihydroimidazo[1,2-a]pyridine and the requisite halide, and employing the procedure of Example 4-B, the following compounds are prepared:

1-(3-chlorobenzyl)-2,3-dihydro-1H-imidazo[1,2-a]pyridinium chloride, m.p. 173°–176° C.

Anal. Calc'd for $C_{14}H_{14}N_2Cl_2$: C, 59.8; H, 5.0; N, 10.0. Found: C, 59.7; H, 5.1; N, 9.9.

1-(2,4-dichlorobenzyl)-2,3-dihydro-1H-imidazo[1,2-a]pyridinium chloride, m.p. 227°–229° C.

Anal. Calc'd for $C_{14}H_{13}N_2Cl_3$: C, 53.3; H, 4.2; N, 8.9. Found: C, 53.2; H, 4.1; N, 9.1.

1-(2,6-dichlorobenzyl)-2,3-dihydro-1H-imidazo[1,2-a]pyridinium chloride, m.p. 254°–256° C.

Anal. Calc'd for $C_{14}H_{13}N_2Cl_3$: C, 53.3; H, 4.2; N, 8.9. Found: C, 53.0; H, 4.3; N, 9.0.

1-(2-chlorobenzyl)-2,3-dihydro-1H-imidazo[1,2-a]pyridinium chloride, m.p. 258°–261° C.

Anal. Calc'd for $C_{14}H_{14}N_2Cl_2$: C, 59.8; H, 5.0; N, 10.0. Found: C, 59.7; H, 5.0; N, 10.0.

1-(4-chlorobenzyl)-2,3-dihydro-1H-imidazo[1,2-a]pyridinium chloride hemihydrate, m.p. 181°–183° C.

Anal. Calc'd for $C_{14}H_{14}N_2Cl_2.\frac{1}{2} H_2O$: C, 57.9; H, 5.2; N, 9.7. Found: C, 57.6; H, 4.8; N, 9.6.

1-(4-methoxybenzyl)-2,3-dihydro-1H-imidazo[1,2-a]pyridinium chloride hemihydrate, m.p. 163°–165° C.

Anal. Calc'd for $C_{15}H_{17}ON_2Cl.\frac{1}{2} H_2O$: C, 63.1; H, 6.3; N, 9.8. Found: C, 62.8; H, 6.1; N, 9.9.

EXAMPLE 6

Employing the procedure of Example 4-B and starting with the 2,3-dihydroimidazo[1,2-a]pyridine and the appropriate halide, the following quaternary salts are synthesized:

| R₃ | X |
|---|---|
| 2,4-dichlorobenzyl | Cl |
| 4-cyanobenzyl | Br |
| 2,4-dibromobenzyl | Cl |
| 2-bromobenzyl | Br |
| 2-fluorobenzyl | Cl |
| 4-fluorobenzyl | Br |
| 3-trifluoromethylbenzyl | Cl |
| 4-phenylbenzyl | Br |
| 4-sulfamoylbenzyl | Br |
| 4-methylsulfonylbenzyl | Br |
| 4-(dimethylsulfamoyl)benzyl | Br |
| 1-naphthylmethyl | Cl |
| 2-naphthylmethyl | Br |

-continued

| R₃ | X |
|---|---|
| 2-phenylethyl | Br |
| 2,3-dichlorobenzyl | Cl |
| 3,5-dichlorobenzyl | Cl |
| 2-methoxybenzyl | Br |
| 3-methoxybenzyl | Cl |
| 3-cyanobenzyl | I |
| 3-fluorobenzyl | Br |
| 3-phenylbenzyl | Cl |
| 3-sulfamoylbenzyl | Cl |
| 2-methylsulfonylbenzyl | Cl |
| 4-trifluoromethylbenzyl | Br | and

| R₂ | X |
|---|---|
| 3-furylmethyl | Br |

-continued

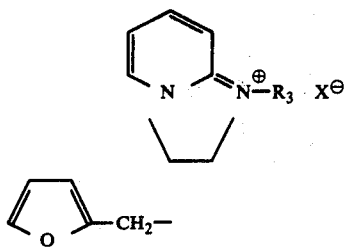

Cl

EXAMPLE 7

1-Benzyl-6-chloroimidazo[1,2-a]pyridinium bromide

A solution of 2.3 g. of 6-chloroimidazo[1,2-a]pyridine and 3.42 g. of α-bromotoluene in 40 ml. of dry acetonitrile is heated at reflux temperatures overnight. The solution is cooled and 35 ml. of diethyl ether added. The precipitated solids are collected and twice recrystallized from isopropanol/diethyl ether, 3.8 g., m.p. 193°–195° C.

Anal. Calc'd for $C_{14}H_{12}N_2ClBr$: C, 52.0; H, 3.7; N, 8.7. Found: C, 52.0; H, 3.8; N, 8.8.

EXAMPLE 8

The procedure of Example 7 is repeated, starting with the requisite reagents, to give the following quaternary salts:

1-(2-chlorobenzyl)-6-chloroimidazo[1,2-a]pyridinium chloride, m.p. 242°–245° C.

Anal. Calc'd for $C_{14}H_{11}N_2Cl_3$: C, 53.6; H, 3.5; N, 8.9. Found: C, 53.6; H, 3.6; N, 8.8.

1-(2,4-dichlorobenzyl)-6-chloroimidazo[1,2-a]pyridinium chloride monohydrate, m.p. 90°–110° C.

Anal. Calc'd for $C_{14}H_{10}N_2Cl_4.H_2O$: C, 45.9; H, 3.3; N, 7.7. Found: C, 45.7; H, 3.7; N, 7.2.

1-benzyl-8-benzyloxyimidazo[1,2-a]pyridinium bromide, m.p. 206°–209° C.

Anal. Calc'd for $C_{21}H_{19}N_2OBr$: C, 63.8; H, 4.8; N, 7.1. Found: C, 64.0; H, 4.8; N, 7.1.

1-(2-chlorobenzyl)-8-benzyloxyimidazo[1,2-a]pyridinium chloride hemihydrate, m.p. 209°–212° C.

Anal. Calc'd for $C_{21}H_{18}ON_2Cl_2.\frac{1}{2} H_2O$: C, 64.0; H, 4.9; N, 7.1. Found: C, 63.8; H, 4.3; N, 7.0.

1-(2,4-dichlorobenzyl)-8-benzyloxyimidazo[1,2-a]pyridinium chloride monohydrate, m.p. 216°–218° C.

Anal. Calc'd for $C_{21}H_{17}ON_2Cl_3$: C, 57.6; H, 4.4; N, 6.4. Found: C, 57.4; H, 3.8; N, 6.3.

1-benzyl-5-chloroimidazo[1,2-a]pyridinium bromide, m.p. 223°–226° C.

Anal. Calc'd for $C_{14}H_{12}N_2BrCl$: C, 52.0; H, 3.7; N, 8.7. Found: C, 51.7; H, 3.7; N, 8.7.

1-(2-chlorobenzyl)-5-chloroimidazo[1,2-a]pyridinium chloride, m.p. 191°–194° C.

Anal. Calc'd for $C_{14}H_{11}N_2Cl_3$: C, 53.6; H, 3.5; N, 8.9. Found: C, 53.3; H, 3.5; N, 9.0.

1-(2,4-dichlorobenzyl)-5-chloroimidazo[1,2-a]pyridinium chloride, m.p. 216°–218° C.

Anal. Calc'd for $C_{14}H_{10}N_2Cl_4$: C, 48.3; H, 2.9; N, 8.1. Found: C, 48.3; H, 3.1; N, 8.0.

1-benzyl-5-benzyloxyimidazo[1,2-a]pyridinium bromide, m.p. 109°–115° C.

Anal. Calc'd for $C_{21}H_{19}ON_2Br$: C, 63.8; H, 4.8; N, 7.1. Found: C, 63.8; H, 4.9; N, 7.0.

1-benzyl-5-methoxyimidazo[1,2-a]pyridinium bromide, m.p. 95°–100° C.

Anal. Calc'd for $C_{15}H_{15}ON_2Br$: C, 56.4; H, 4.7; N, 8.8. Found: C, 56.8; H, 5.0; N, 9.0.

1-(2-chlorobenzyl)-5-methoxyimidazo[1,2-a]pyridinium chloride, m.p. 150° C.

Anal. Calc'd for $C_{15}H_{14}ON_2Cl_2$: C, 58.3; H, 4.6; N, 7.1. Found: C, 58.2; H, 4.7; N, 9.3.

EXAMPLE 9

The procedure of Example 7 is repeated, starting with the appropriate substituted imidazo[1,2-a]pyridine and halide, to provide the following quaternary salt:

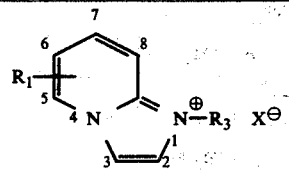

| $R_1$ | $R_3$ | X |
|---|---|---|
| 6-Cl— | 2-FC$_6$H$_4$CH$_2$— | Cl |
| 6-Cl— | 4-NCC$_6$H$_4$CH$_2$— | Cl |
| 6-Cl— | 2-BrC$_6$H$_4$CH$_2$— | Br |
| 8-φCH$_2$O— | 3,5-Cl$_2$C$_6$H$_3$CH$_2$— | Cl |
| 8-φCH$_2$O— | 3-BrC$_6$H$_4$CH$_2$— | Br |
| 8-φCH$_2$O— | 3-CF$_3$C$_6$H$_4$CH$_2$— | Cl |
| 8-φCH$_2$O— | 4-φC$_6$H$_4$CH$_2$— | Br |
| 5-CH$_3$O— | 3-CF$_3$C$_6$H$_4$CH$_2$— | Cl |
| 5-CH$_3$O— | 3-NCC$_6$H$_4$CH$_2$— | I |
| 5-CH$_3$O— | 4-(CH$_3$)$_2$NSO$_2$C$_6$H$_4$CH$_2$— | Br |
| 5-CH$_3$O— | 4-CH$_3$OC$_6$H$_4$CH$_2$— | Cl |
| 5-φCH$_2$O— | 3-ClC$_6$H$_4$CH$_2$— | Cl |
| 5-φCH$_2$O— | 4-BrC$_6$H$_4$CH$_2$— | Br |
| 5-φCH$_2$O— | 3-CH$_3$OC$_6$H$_4$CH$_2$— | Cl |
| 5-φCH$_2$O— | 3,5-Cl$_2$C$_6$H$_3$CH$_2$— | Cl |
| 5-φCH$_2$O— | 4-FC$_6$H$_4$CH$_2$— | Br |
| 7-Cl— | C$_6$H$_5$CH$_2$— | Cl |
| 7-Cl— | 2,4-Cl$_2$C$_6$H$_3$CH$_2$— | Cl |
| 7-Cl— | 3-BrC$_6$H$_4$CH$_2$— | Br |
| 7-Cl— | 3-NCC$_6$H$_4$CH$_2$— | I |
| 7-Cl— | 4-φC$_6$H$_4$CH$_2$— | Br |
| 6-φCH$_2$O— | 2-FC$_6$H$_4$CH$_2$— | Cl |
| 6-φCH$_2$O— | 2-BrC$_6$H$_4$CH$_2$— | Br |
| 6-φCH$_2$O— | 3-φC$_6$H$_4$CH$_2$— | Cl |
| 6-φCH$_2$O— | β-naphthylmethyl- | Br |

EXAMPLE 10

1-(2,4-Dichlorobenzyl)-2,3-dihydro-1H-6,8-dichloroimidazo[1,2-a]pyridinium chloride A mixture of 1.89 g. of 2,3-dihydro-6,8-dichloroimidazo[1,2-a]pyridine and 4.89 g. of 2,4-dichlorobenzyl chloride in 75 ml. of dry acetonitrile is heated at reflux temperatures overnight. Diethyl ether (35 ml.) is added to the cooled reaction mixture, and the resulting precipitated solids filtered and dried. The desired product is further purified by recrystallization from acetonitrile.

EXAMPLE 11

Starting with the requisite dihydroimidazo[1,2-a]pyridine and appropriate halide, and employing the procedure of Example 10, the following quaternary salts are prepared:

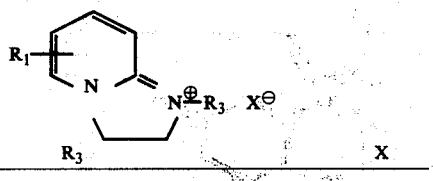

| $R_1$ | $R_3$ | X |
|---|---|---|

-continued

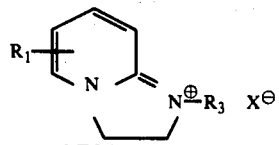

| $R_1$ | $R_2$ | X |
|---|---|---|
| 6-Cl— | 2-FC$_6$H$_4$CH$_2$— | Cl |
| 6-Cl— | 2-BrC$_6$H$_4$CH$_2$— | Br |
| 8-φCH$_2$O— | 3-BrC$_6$H$_4$CH$_2$— | Br |
| 8-φCH$_2$O— | 4-φC$_6$H$_4$CH$_2$— | Br |
| 5-CH$_3$O— | 3-NCC$_6$H$_4$CH$_2$— | I |
| 5-CH$_3$O— | 4-CH$_3$OC$_6$H$_4$CH$_2$— | Cl |
| 5-φCH$_2$O— | 3-CH$_3$OC$_6$H$_4$CH$_2$— | Cl |
| 5-φCH$_2$O— | 3,5-Cl$_2$C$_6$H$_3$CH$_2$— | Cl |
| 5-φCH$_2$O— | 4-FC$_6$H$_4$CH$_2$— | Br |
| 7-Cl— | C$_6$H$_5$CH$_2$— | Cl |
| 7-Cl— | 3-BrC$_6$H$_4$CH$_2$— | Br |
| 7-Cl— | 4-φC$_6$H$_4$CH$_2$— | Br |
| 6-φCH$_2$O— | 2-FC$_6$H$_4$CH$_2$— | Cl |
| 6-φCH$_2$O— | 2-BrC$_6$H$_4$CH$_2$— | Br |
| 6-φCH$_2$O— | β-naphthylmethyl | Br |
| and $R_1$ | $R_2$ | X |
| 5-Cl— | 8-quinolylmethyl- | Cl |
| 7-Cl— | 3-furfuryl- | Br |

EXAMPLE 12

1-Methyl-2-(4-methoxyphenyl)imidazo[1,2-a]pyridinium iodide

A. 2-(4-methoxyphenyl)imidazo[1,2-a]pyridine

A mixture of 25.2 g. of sodium bicarbonate, 12.3 g. of 2-aminopyridine and 30 g. of α-bromo-p-methoxyacetophenone in 100 ml. of water and 550 ml. of absolute ethanol is heated at reflux temperatures for 1.5 hrs. The reaction mixture is concentrated under reduced pressure to a yellow solid, which is partitioned between chloroform and water. The organic layer is separated, dried over sodium sulfate. Removal of the chloroform in vacuo leaves the crude intermediate as a yellow solid. Recrystallization from ethanolwater give 15.2 g. of the desired material, m.p. 131–134° C.

B. 1-methyl-2-(4-methoxyphenyl)imidazo[1,2-a]pyridinium iodide

To 2.23 g. of 2-(4-methoxyphenyl)imidazo[1,2-a]pyridine in 50 ml. of acetonitrile is added 2.84 g. of methyl iodide, and the resulting reaction mixture refluxed for 3 hrs. Additional methyl iodide (2 ml.) is added and reflux continued for one hour. The solids which precipitate on cooling are filtered and partially dissolved in boiling isopropanol and filtered. The isopropanol filtrate is cooled and treated with diethyl ether. The crystallized product is filtered and dried to give 1.03 g., m.p. 194–196° C.

Anal. Calc'd for C$_{15}$H$_{15}$N$_2$OI: C, 49.2; H, 4.1; N, 7.7. Found: C, 48.9; H, 4.2; N, 7.7.

EXAMPLE 13

Employing the procedure of Example 12-B, and starting with the appropriate 2-phenylimidazo[1,2-a]pyridine and methyl halide, the following compounds are synthesized:

1-methyl-2-(4-bromophenyl)imidazo[1,2-a]pyridinium iodide, m.p. 237–241° C.

Anal. Calc'd for C$_{14}$H$_{12}$N$_2$BrI: C, 40.5; H, 2.9; N, 6.8. Found: C, 40.5; H, 3.0; N, 6.8.

1-methyl-2-(4-tolyl)imidazo[1,2-a]pyridinium iodide, m.p. 218–220° C.

Anal. Calc'd for C$_{15}$H$_{15}$N$_2$I: C, 51.4; H, 4.3; N, 8.0. Found: C, 51.6; H, 4.3; N, 8.1.

1-methyl-2-(4-chlorophenyl)imidazo[1,2-a]pyridinium iodide, m.p. 240–243° C.

Anal. Calc'd for C$_{14}$H$_{12}$N$_2$ClI: C, 45.4; H, 3.3; N, 7.6. Found: C, 45.9; H, 3.4; N, 7.7.

1-methyl-2-(2,4-dichlorophenyl)imidazo[1,2-a]pyridinium iodide, m.p. 233–234° C.

Anal. Calc'd for C$_{14}$H$_{11}$N$_2$Cl$_2$I: C, 41.5; H, 2.7; N, 6.9. Found: C, 41.6; H, 2.8; N, 6.7.

EXAMPLE 14

1-Benzylimidazo[1,5-a]pyridinium bromide

A. 2-formamidomethylpyridine

A mixture of 32.4 g. of 2-aminomethylpyridine and 96 ml. of 97% formic acid is heated under reflux for 3.5 hrs. The resulting solution is subjected to vacuum distillation, the desired product being isolated as the fraction boiling at 120° C./0.03 mm, 37.3 g. The product which is isolated as a yellow oil crystallized to a solid having a melting point at about room temperature.

B. imidazo[1,5-a]pyridine

To 13.6 g. of 2-formamidomethylpyridine in a round-bottom flask is added 25 ml. of phosphorous oxychloride. Following the exothermic reaction, the reaction mixture is cooled to room temperature, and quenched on crushed ice. The aqueous mixture is treated with sufficient 20% aqueous sodium hydroxide solution to provide a pH of 9-10, and the liberated product extracted into chloroform (3 × 300 ml.). The extracts are combined, dried over sodium sulfate and concentrated to a light brown oil, 14.0 g.

C. 1-benzylimidazo[1,5-a]pyridinium bromide

Imidazo[1,5-a]pyridine (3.9 g.) in 100 ml. of dry acetonitrile is treated with 6.8 g. of α-bromotoluene, and the resulting reaction mixture heated under reflux for 3 hrs. The solution is cooled and diluted with 250 ml. of diethyl ether. The resulting precipitate is filtered and recrystallized from isopropanol-diethyl ether, 7.92 g., m.p. 172–176° C.

Anal. Calc'd for C$_{14}$H$_{13}$N$_2$Br: C, 58.2; H, 4.5; N, 9.7. Found: C, 58.3; H, 4.7; N, 9.7.

EXAMPLE 15

The procedure of Example 14-C is repeated, starting with the appropriate halide and imidazo[1,5-a]pyridine, to provide the indicated quaternary compounds:

2-(2-chlorobenzyl)imidazo[1,5-a]pyridinium chloride, m.p. 153–155° C.

Anal. Calc'd for C$_{14}$H$_{12}$N$_2$Cl$_2$: C, 60.2; H, 4.3; N, 10.0. Found: C, 60.0; H, 4.6; N, 9.7.

2-(2,4-dichlorobenzyl)imidazo[1,5-a]pyridinium chloride hydrate, m.p. 202–207° C.

Anal. Calc'd for C$_{14}$H$_{11}$N$_2$Cl$_3$.¼ H$_2$O: C, 52.9; H, 3.6; N, 8.8. Found: C, 53.0; H, 3.8; N, 8.6.

2-methylimidazo[1,5-a]pyridinium iodide, m.p. 160° C.

Anal. Calc'd for C$_8$H$_9$N$_2$I: C, 36.9; H, 3.5; N, 10.8. Found: C, 37.1; H, 3.6; N, 10.9.

1-phenyl-2-methylimidazo[1,5-a]pyridinium iodide acetonitrile solvate, m.p. 84–95° C.

Anal. Calc'd for C$_{14}$H$_{13}$N$_2$I.CH$_3$CN: C, 51.0; H, 4.3; N, 11.1. Found: C, 50.9; H, 4.4; N, 10.7.

2-methyl-3-phenylimidazo[1,5-a]pyridinium iodide, m.p. 197–199° C.

Anal. Calc'd for $C_{14}H_{13}N_2I$: C, 50.0; H, 3.9; N, 8.3. Found: C, 50.1; H, 4.0; N, 8.3.

2-benzylimidazo[1,5-a]quinolinium bromide, m.p. 224–226° C.

Anal. Calc'd for $C_{18}H_{15}N_2Br$: C, 63.7; H, 4.5; N, 8.3. Found: C, 63.4; H, 4.8; N, 8.2.

2-(2-chlorobenzyl)imidazo[1,5-a]quinolinium chloride, m.p. 223–225° C.

Anal. Calc'd for $C_{18}H_{14}N_2Cl_2$: C, 65.7; H, 4.3; N, 8.5. Found: C, 65.3; H, 4.2; N, 8.8.

2-(2,4-dichlorobenzyl)imidazo[1,5-a]quinolinium chloride, m.p. 263–266° C.

Anal. Calc'd for $C_{18}H_{13}N_2Cl_3$: C, 59.5; H, 3.6; N, 7.7. Found: C, 59.3; H, 3.9; N, 7.8.

EXAMPLE 16

The process of Example 14-C is again repeated employing as starting reagents the requisite halide and imidazo[1,5-a]pyridine or -quinoline, to provide the following products:

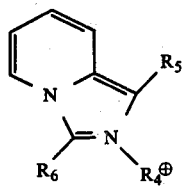

| $R_4$ | $R_5$ | $R_6$ | X |
|---|---|---|---|
| 4-ClC$_6$H$_4$CH$_2$— | H | H | Cl |
| 3,4-Cl$_2$C$_6$H$_3$CH$_2$— | H | H | Cl |
| 2,6-Cl$_2$C$_6$H$_3$CH$_2$— | H | H | Cl |
| C$_2$H$_5$— | H | φ | I |
| n-C$_3$H$_7$— | H | φ | Br |
| C$_2$H$_5$— | φ | H | I |
| i-C$_3$H$_7$— | φ | H | I |
| C$_6$H$_5$CH$_2$— | φ | H | Br |
| 4-ClC$_6$H$_4$CH$_2$— | φ | H | Cl |
| 3,5-Cl$_2$C$_6$H$_3$CH$_2$— | φ | H | Cl |
| 2,4-Cl$_2$C$_6$H$_3$CH$_2$— | φ | H | Cl |
| 2-ClC$_6$H$_4$CH$_2$— | φ | H | Cl |
| 2-ClC$_6$H$_4$CH$_2$— | H | φ | Cl |
| 3,4-Cl$_2$C$_6$H$_3$CH$_2$— | H | φ | Cl |
| C$_6$H$_5$CH$_2$— | H | φ | Br |
| 3-ClC$_6$H$_4$CH$_2$— | H | φ | Cl | and

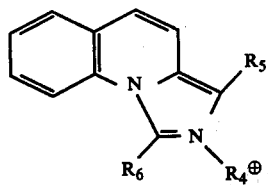

| $R_4$ | $R_5$ | $R_6$ | X |
|---|---|---|---|
| 4-ClC$_6$H$_4$CH$_2$— | H | H | Cl |
| 2,6-Cl$_2$C$_6$H$_3$CH$_2$— | H | H | Cl |
| 3,5-Cl$_2$C$_6$H$_3$CH$_2$— | H | H | Cl |
| CH$_3$— | φ | H | I |
| C$_2$H$_5$— | φ | H | Br |
| i-C$_3$H$_7$— | φ | H | Br |
| C$_6$H$_5$CH$_2$— | φ | H | Cl |
| 4-ClC$_6$H$_4$CH$_2$— | φ | H | Cl |
| 2,4-Cl$_2$C$_6$H$_3$CH$_2$— | φ | H | I |
| CH$_3$— | H | φ | Br |
| n-C$_3$H$_7$— | H | φ | Br |
| C$_6$H$_5$CH$_2$— | H | φ | Cl |
| 3-ClC$_6$H$_4$CH$_2$— | H | φ | Cl |
| 4-ClC$_6$H$_4$CH$_2$— | H | φ | Cl |
| 3,5-Cl$_2$C$_6$H$_3$CH$_2$— | H | φ | Cl |

EXAMPLE 17

1-Benzyl-1H-imidazo[2,1-a]isoquinolinium bromide

A solution of 600 mg. of imidazo[2,1-a]isoquinoline and 610 mg. of α-bromotoluene in 25 ml. of acetonitrile is heated under reflux for two days. The reaction mixture is subsequently cooled and diluted with diethyl ether. The resulting precipitate is recrystallized from isopropanol-diethyl ether and then twice from isopropanol to give 570 mg., m.p. 247–249° C.

Anal. Calc'd for $C_{18}H_{15}N_2Br$: C, 63,7; H, 4.5; N, 8.3. Found: C, 63.6; H, 4.8; N, 8.3.

Similarly is prepared:

1-(2-chlorobenzyl)-1H-imidazo[2,1-a]isoquinolinium chloride hydrate, m.p. 226–229° C.

Anal. Calc'd for $C_{18}H_{14}N_2Cl_2 \cdot H_2O$: C, 62.3; H, 4.6; N, 8.1. Found: C, 62.0; H, 4.8; N, 8.0.

EXAMPLE 18

2-Benzylimidazo[5,1-a]isoquinolinium bromide

Following the general procedure of Example 17, 1.68 g. of imidazo[5,1-a]isoquinoline and 2.05 g. of α-bromotoluene in 50 ml. of acetonitrile is heated at reflux temperature overnight. Diethyl ether (25 ml.) is added to the cooled reaction mixture and the resulting solids filtered. Recrystallization from isopropanol-diethyl ether provides 2.7 g. of the purified product, m.p. 231–234° C.

Anal. Calc'd for $C_{18}H_{15}N_2Br$: C, 63.7; H, 4.5; N, 8.3. Found: C, 63.6; H, 4.6; N, 8.1.

Similarly are prepared:

2-(2-chlorobenzyl)imidazo[5,1-a]isoquinolinium chloride hydrate, m.p. 215–217° C.

Anal. Calc'd for $C_{18}H_{14}N_2Cl_2 \cdot \frac{1}{4} H_2O$: C, 64.8; H, 4.4; N, 8.4. Found: C, 64.6; H, 4.4; N, 8.2.

2-(2,4-dichlorobenzyl)imidazo[5,1-a]isoquinolinium chloride hydrate, m.p. 258–261° C.

Anal. Calc'd for $C_{18}H_{13}N_2Cl_3 \cdot \frac{1}{4} H_2O$: C, 58.7; H, 3.8; N, 7.6. Found: C, 58.8; H, 3.8; N, 7.5.

EXAMPLE 19

1-Benzylpyrazolo[1,5-a]pyridinium bromide

Pyrazolo[1,5-a]pyridine (1.0 g.) and 2.05 g. of α-bromotoluene in 30 ml. of acetonitrile are heated under reflux overnight. The reaction mixture is cooled and diluted with 50 ml. of diethyl ether. The oil which initially separated from solution crystallizes on stirring, and is subsequently recrystallized from isopropanol-diethyl ether, 1.3 g. m.p. 135–138° C.

Anal. Calc'd for $C_{14}H_{13}N_2Br$: C, 58.2; H, 4.5; N, 9.7. Found: C, 58.3; H, 4.6; N, 9.6.

Similarly are prepared:

1-(2-chlorobenzyl)pyrazolo[1,5-a]pyridinium chloride hydrate, m.p. 121–123° C.

Anal. Calc'd for $C_{14}H_{12}N_2Cl_2 \cdot H_2O$: C, 56.6; H, 4.8; N, 9.4. Found: C, 55.9; H, 4.6; N, 9.3.

1-(2,4-dichlorobenzyl)pyrazolo[1,5-a]pyridinium chloride hydrate, m.p. 125–130° C.

Anal. Calc'd for $C_{14}H_{11}N_2Cl_3 \cdot H_2O$: C, 50.7; H, 4.0; N, 8.5. Found: C, 50.8; H, 4.0; N, 8.4.

EXAMPLE 20

2-Benzylpyrrolo[1,2-a]pyrazinium bromide

A reaction mixture comprising 2.0 g. of pyrrolo[1,2-a]pyrazine and 4.27 g. of α-bromotoluene in 50 ml. of dry acetonitrile is stirred at room temperature overnight. Diethyl ether (50 ml.) is added to the suspension and the solids filtered. Recrystallization from isopropanol-diethyl ether gives 3.48 g. of the purified product, m.p. 173–177° C.

Anal. Calc'd for $C_{14}H_{13}N_2Br$: C, 58.2; H, 4.5; N, 9.7. Found: C, 58.0; H, 4.6; N, 9.6.

Similarly are prepared:

2-(2-chlorobenzyl)pyrrolo[1,2-a]pyrazinium chloride hydrate, m.p. 188–190° C.

Anal. Calc'd for $C_{14}H_{12}N_2Cl_2 \cdot \frac{1}{2} H_2O$: C, 58.4; H, 4.6; N, 9.7. Found: C, 58.6; H, 4.6; N, 9.7.

2-(2,4-dichlorobenzyl)pyrrolo[1,2-a]pyrazinium chloride hydrate, m.p. 208–211° C.

Anal. Calc'd for $C_{14}H_{11}N_2Cl_3 \cdot \frac{1}{4} H_2O$: C, 52.9; H, 3.6; N, 8.8. Found: C, 52.7; H, 3.7; N, 8.7.

5-benzylpyrrolo[1,2-a]quinoxalinium bromide hydrate, m.p. 204–206° C.

Anal. Calc'd for $C_{18}H_{15}N_2Br \cdot H_2O$: C, 60.5; H, 4.8; N, 7.8. Found: C, 60.9; H, 4.7; N, 7.8.

5-(2-chlorobenzyl)pyrrolo[1,2-a]quinoxalinium chloride hydrate, m.p. 228° C. (dec.).

Anal. Calc'd for $C_{18}H_{14}N_2Cl_2 \cdot \frac{1}{4} H_2O$: C, 64.8; H, 4.4; N, 8.4. Found: C, 64.9; H, 4.4; N, 8.2.

5-(4-chlorobenzyl)pyrrolo[1,2-a]quinoxalinium chloride hydrate, m.p. 215° C. (dec.).

Anal. Calc'd for $C_{18}H_{14}N_2Cl_2 \cdot \frac{3}{4} H_2O$: C, 63.1; H, 4.6; N, 8.2. Found: C, 63.1; H, 4.5; N, 8.0.

EXAMPLE 21

Following the procedure of Example 20, and starting with the appropriate halide and heterocyclic base, the indicated quaternary compounds are prepared:

5-(2,4-dichlorobenzyl)pyrrolo[1,2-a]quinoxalinium chloride; 2-(4-chlorobenzyl)pyrrolo[1,2-a]pyrazinium chloride; 1-(4-chlorobenzyl)pyrazolo[1,5-a]pyridinium bromide; 1-(2,4-dichlorobenzyl)-1H-imidazo[2,1-a]isoquinolinium chloride; 1-(4-chlorobenzyl)-1H-imidazo[2,1-a]isoquinolinium bromide; and 2-(4-chlorobenzyl)imidazo[5,1-a]isoquinolinium bromide.

EXAMPLE 22

1-Benzylimidazo[1,2-a]pyridinium Salts

An ion exchange column approximately 1 × 24 inches is packed with Amberlite 1R 400 in 2N aqueous sodium hydroxide solution. The column is thoroughly washed successively with 3 l. of 1N aqueous sodium hydroxide, 3 l. 5N aqueous sodium hydroxide, 2 l. 2.5N aqueous sodium hydroxide, and 3 l. 5N aqueous sodium hydroxide. The column is then washed with dionized water until the washings are neutral to pH paper.

Acetate Salt

One gram of 1-benzylimidazo[1,2-a]pyridinium bromide dissolved in water is passed through the prepared column. Deonized water is then passed through the column until all basic fractions (via pH paper) have been collected. To the combined basic fractions is added 10 ml. of acetic acid and the resulting solution concentrated to dryness in vacuo. The resulting oil crystallizes when triturated with isopropanol-ethyl acetate. The acetate salt is very hydroscopic.

Sulfate Salt

As in the description for the preparation of the acetate salt, 1 g. of 1-benzylimidazo[1,2-a]pyridinium bromide dissolved in water is passed through the aforementioned prepared column, the basic fractions resulting from the dionized water washes being collected (50 ml.). To these combined basic fractions is added 170 mg. of sulfuric acid and the resulting solution concentrated under reduced pressure to dryness, 680 mg., m.p. 257° C.

Anal. Calc'd for $C_{28}H_{26}N_4O_4S$: C, 65.4; H, 5.1; N, 10.9. Found: C, 65.3; H, 5.0; N, 10.5.

Iodide Salt

Employing the same general procedure, 850 mg. of 1-benzylimidazo[1,2-a]pyridinium bromide gave 870 mg. of the corresponding iodide salt, m.p. 134°–136° C.

Anal. Calc'd for $C_{14}H_{13}N_2I$: C, 50.0; H, 3.9; N, 8.3. Found: C, 49.9; H, 3.9; N, 8.1.

Tosylate Salt

Employing the same procedure, 850 mg. of 1-benzylimidazo [1,2-a]pyridinium bromide gave 850 mg. of the corresponding tosylate salt, m.p. 156°–158° C.

Anal. Calc'd for $C_{21}H_{20}O_3N_2S$: C, 66.3; H, 5.3; N, 7.4. Found: C, 65.9; H, 5.3; N, 7.4.

EXAMPLE 23

Hypoglycemic Testing

The hypoglycemic testing of the compounds of the present invention is carried out by a standard procedure, and comprises grouping eight, Hartley strain, male guinea pigs which have been fasted 18–24 hrs. in each group. Blood samples are obtained from the pentobarbital-anesthetized animals by cardiac puncture. Each of the eight animals is dosed i.p. with a given dose of the test compound. Blood samples are taken 1, 2, and 4 hours following the dozing, and the venous blood diluted 1:10 with saline and assayed for blood sugar levels on an Auto-Analyzer, the levels being expressed as mg.%. The activity for the test compound is expressed as the percent lowering of the blood sugar at the 1, 2, and 4 hr. when compared with the blood sugar level of a group of eight control animals which have been similarly dosed with a saline solution.

The following representative quaternary salts were tested as hypoglycemic agents following the above mentioned procedure, and found to be active at the indicated dose level.

| | | | | % Fall Blood Sugar Level | | |
|---|---|---|---|---|---|---|
| | | | Dose | | | |
| $R_1$ | $R_3$ | X | mg./kg. | $T_1$ | $T_2$ | $T_4$ |
| H | $C_6H_5CH_2-$ | I | 30 | 18 | 55 | 65 |
| H | $2\text{-}ClC_6H_4CH_2-$ | Cl | 25 | 14 | 27 | 57 |
| H | $2,6\text{-}Cl_2C_6H_3CH_2-$ | Cl | 50 | 4 | 16 | 49 |
| H | $4\text{-}CH_3OC_6H_4CH_2-$ | Cl | 50 | 19 | 51 | 60 |
| H | $4\text{-}FC_6H_4CH_2-$ | Br | 50 | 33 | 70 | 89 |
| H | $4\text{-}BrC_6H_4CH_2-$ | Br | 50 | 51 | 84 | — |
| H | $3\text{-}CF_3C_6H_4CH_2-$ | Cl | 50 | 10 | 25 | 80 |
| H | $4\text{-}\phi C_6H_4CH_2-$ | Br | 50 | 45 | 53 | 46 |
| H | $C_6H_5CH_2CH_2-$ | Br | 50 | 37 | 75 | 80 |
| $5\text{-}CH_3O$ | $C_6H_5CH_2-$ | Br | 50 | 31 | 70 | 86 |
| $8\text{-}\phi CH_2O$ | $2\text{-}ClC_6H_4CH_2-$ | Cl | 50 | 17 | 70 | — |
| $6\text{-}Cl$ and $R_1$ | $2\text{-}ClC_6H_4CH_2-$ $R_2$ | Cl | 50 | 5 | 32 | 35 |
| H | 2-furfuryl- | Cl | 50 | 38 | 71 | 67 |
| H | 8-quinolylmethyl- | Br | 50 | 14 | 68 | 86 |

-continued

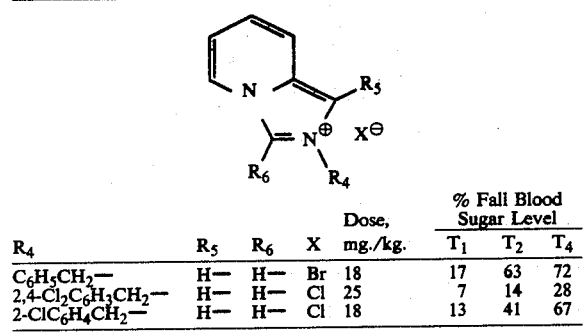

| R$_4$ | R$_5$ | R$_6$ | X | Dose, mg./kg. | % Fall Blood Sugar Level T$_1$ | T$_2$ | T$_4$ |
|---|---|---|---|---|---|---|---|
| C$_6$H$_5$CH$_2$— | H— | H— | Br | 18 | 17 | 63 | 72 |
| 2,4-Cl$_2$C$_6$H$_3$CH$_2$— | H— | H— | Cl | 25 | 7 | 14 | 28 |
| 2-ClC$_6$H$_4$CH$_2$— | H— | H— | Cl | 18 | 13 | 41 | 67 |

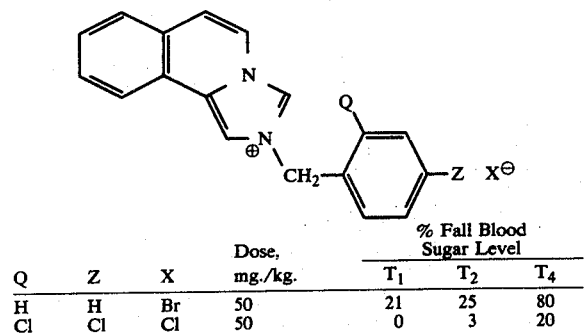

| Q | Z | X | Dose, mg./kg. | % Fall Blood Sugar Level T$_1$ | T$_2$ | T$_4$ |
|---|---|---|---|---|---|---|
| H | H | Br | 50 | 21 | 25 | 80 |
| Cl | Cl | Cl | 50 | 0 | 3 | 20 |

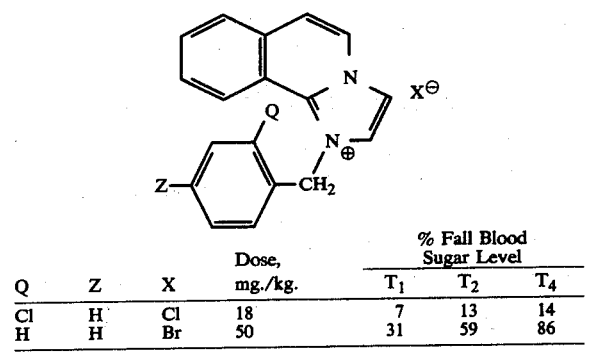

| Q | Z | X | Dose, mg./kg. | % Fall Blood Sugar Level T$_1$ | T$_2$ | T$_4$ |
|---|---|---|---|---|---|---|
| Cl | H | Cl | 18 | 7 | 13 | 14 |
| H | H | Br | 50 | 31 | 59 | 86 |

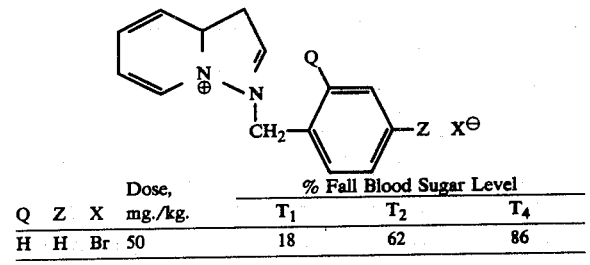

| Q | Z | X | Dose, mg./kg. | % Fall Blood Sugar Level T$_1$ | T$_2$ | T$_4$ |
|---|---|---|---|---|---|---|
| H | H | Br | 50 | 18 | 62 | 86 |

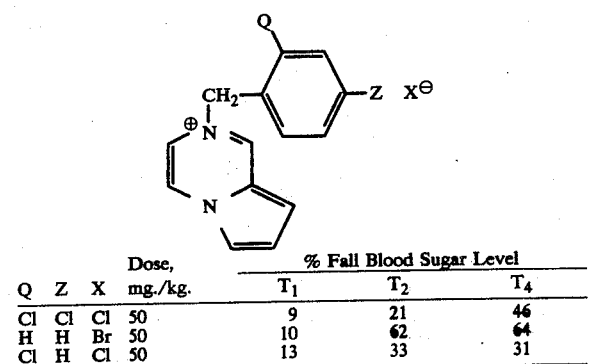

| Q | Z | X | Dose, mg./kg. | % Fall Blood Sugar Level T$_1$ | T$_2$ | T$_4$ |
|---|---|---|---|---|---|---|
| Cl | Cl | Cl | 50 | 9 | 21 | 46 |
| H | H | Br | 50 | 10 | 62 | 64 |
| Cl | H | Cl | 50 | 13 | 33 | 31 |

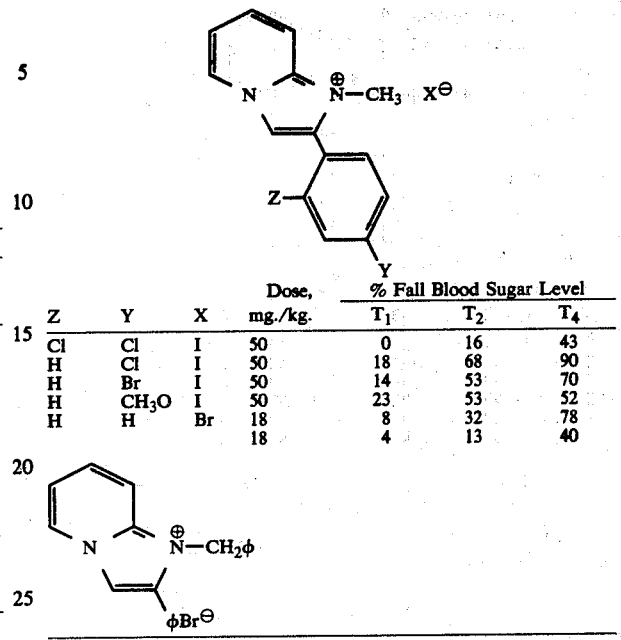

| Z | Y | X | Dose, mg./kg. | % Fall Blood Sugar Level T$_1$ | T$_2$ | T$_4$ |
|---|---|---|---|---|---|---|
| Cl | Cl | I | 50 | 0 | 16 | 43 |
| H | Cl | I | 50 | 18 | 68 | 90 |
| H | Br | I | 50 | 14 | 53 | 70 |
| H | CH$_3$O | I | 50 | 23 | 53 | 52 |
| H | H | Br | 18 | 8 | 32 | 78 |
|   |   |   | 18 | 4 | 13 | 40 |

EXAMPLE 24

Hypoglycemic Activity -
1-benzyl-2-methylimidazo[1,2-a]pyridinium bromide vs.
1-benzylimidazo[1,2-a]pyridinium bromide The known compound, 1-benzyl-2-methylimidazo[1,2-a]pyridinium bromide, reported by Bradsher, et. al., *J. Heterocyclic Chem.*, 2, 331 (1965), is compared with the desmethyl homolog of the present invention by the hypoglycemic testing procedure of Example 23. The results are as follows:

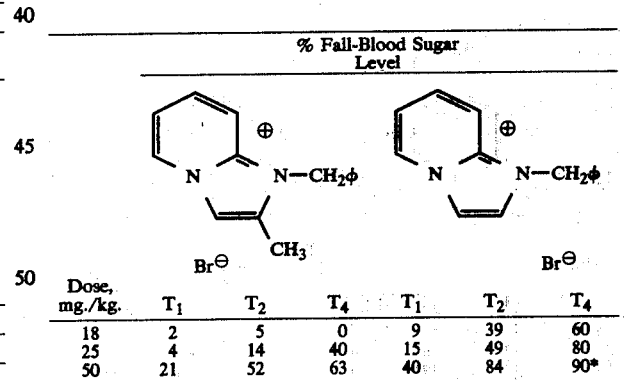

| Dose, mg./kg. | % Fall-Blood Sugar Level | | | | | |
|---|---|---|---|---|---|---|
|  | T$_1$ | T$_2$ | T$_4$ | T$_1$ | T$_2$ | T$_4$ |
| 18 | 2 | 5 | 0 | 9 | 39 | 60 |
| 25 | 4 | 14 | 40 | 15 | 49 | 80 |
| 50 | 21 | 52 | 63 | 40 | 84 | 90* |

*only one animal surviving

The results indicate that the 1-benzylimidazo[1,2-a]pyridinium of the present invention is superior to the known compound in hypoglycemic activity. It is further noted that while the compound of the instant invention is active at 18 mg./kg., the hypolycemic activity of 1-benzyl-2-methylimidazo[1,2-a]pyridinium bromide is indistinguishable from the control group.

PREPARATION A cl I. Imidazo[1,2a]pyridines a. Imidazo[1,2-a]pyridine

A mixture of 47 g. of 2-aminopyridine, 120 g. of 45% chloroacetaldehyde solution in water and 50.4 g. of sodium bicarbonate in 400 ml. of anhydrous ethanol and 100 ml. of water is heated to reflux for 3 hrs. The reaction mixture is cooled, treated with 900 ml. of water and extracted with diethyl ether (3 × 700 ml.). The combined extracts are dried over sodium sulfate and concentrated to a brown oil. Distillation gives 18.8 g. of the desired intermediate as a light yellow oil, b.p. 70° C./0.02 mm.

b. Employing the general procedure of Preparation A-Ia and starting with the appropriate aminopyridine and chloroacetaldehyde or an acetal thereof, the following intermediate imidazo[1,2-a]pyridines are prepared:

6-chloroimidazo[1,2-a]pyridine, 8-benzyloxyimidazo[1,2-a]pyridine, 5-chloroimidazo[1,2-a]pyridine, 7-chloroimidazo[1,2-a]pyridine, 5-methylimidazo[1,2-a]pyridine, 6-methylimidazo[1,2-a]pyridine, 8-methylimidazo[1,2-a]pyridine and 6-benzyloxyimidazo[1,2-a]pyridine.

c. 5-Methoxyimidazo[1,2-a]pyridine

A mixture of 8.08 g. of 5-chloroimidazo[1,2-a]pyridine and 5.4 g. of sodium methoxide in 100 ml. of dimethylformamide is allowed to stir at room temperature overnight. The reaction mixture is poured on to 800 ml of ice and water and extracted with chloroform (3 × 100 ml.). The chloroform extracts are combined, dried over sodium sulfate and concentrated to an oil. The oil is subsequently dissolved in ethylacetate and treated with sufficient hydrogen chloride in ethyl acetate to completely convert to free base to the hydrochloride salt, which is filtered and dried, 8.0 g., m.p. 175°–177° C.

An aqueous solution of 5.55 g. of 5-methoxyimidazo[1,2-]pyridine hydrochloride is made strongly basic by the addition of aqueous sodium hydroxide. The cloudy solution is extracted with methylene chloride (4 × 75 ml.) and the extracts combined and dried over sodium sulfate. Removal of the solvent leaves 5-methoxyimidazole[1,2-a]pyridine as a yellow oil, 4.5 g.

d. Starting with the appropriate halo substituted imidazo[1,2-a]pyridine and alkoxide and employing the procedure of Preparation AI-c, the following intermediates are synthesized:

5-benzyloxyimidazo[1,2-a]pyridine and 8-benzyloxyimidazo[1,2-a]pyridine.

e. 2,3-dihydroimidazo[1,2-a]pyridine

A mixture of 72.5 g. of 2-aminopyridine and 67.0 g. of 2-chloroethanol is heated at 110° for 52 hrs. The mixture is cooled to room temperature and is then treated with water and sufficient solid sodium carbonate to give pH 8. Chloroform (200 ml.) is added and the two-phase system heated until a solution results. The aqueous layer is separated, washed again with chloroform (2 × 100 ml.) and subsequently concentrated to dryness. The residue from the aqueous layer is extracted with ethanol. The insolubles are filtered and the ethanol filtrate is allowed to stand at room temperature overnight. The precipitated solids, comprising 30.5 g. of the product, 1-(2-hydroxyethyl)-2-aminopyridinium chloride are filtered. Evaporation of the filtrate to half volume provides an additional 31.4 g. of the desired material, m.p. 146°–149° C.

Fifty grams of the above-mentioned 1-(2-hydroxyethyl)-2-aminopyridinium chloride is converted into 41.0 g., m.p. 178°–180° C., of the desired product as the hydrobromide salt following the procedure of Burton, et al., *J. Chem. Soc. (Perkins)*, (1972), 1940.

Sixteen grams of the hydrobromide salt in 100 ml. of water is treated with 20 ml. of 20%. (w/v) aqueous sodium hydroxide solution. The resulting solution is concentrated in vacuo to a low volume and extracted with benzene. The benzene layer is separated, dried over sodium sulfate and concentrated to 8.75 g. of a yellow oil which crystallizes to a low melting solid.

f. Following the procedure of Preparation AI-e and starting with the appropriate aminopyridine, the indicated intermediate 2,3-dihydroimidazo[1,2-a]pyridine compounds are prepared:

6-chloro-2,3-dihydroimidazo[1,2-a]pyridine, 8-benzyloxy-2,3-dihydroimidazo[1,2-a]-pyridine, 5-chloro-2,3-dihydroimidazo[1,2-a]pyridine, 5-methoxy-2,3-dihydroimidazo[1,2-a]pyridine, 5-benzyloxy-2,3-dihydroimidazo[1,2-a]pyridine and 7-chloro-2,3-dihydroimidazo[1,2-a]pyridine.

g. 2-(2,4-dichlorophenyl)imidazo[1,2-a]pyridine

A reaction mixture comprising 25.2 g. of sodium bicarbonate, 18.84 g. of 2-aminopyridine and 44.7 g. of 2,2',4-trichloroacetophenone in 100 ml. of water and 550 ml. of ethanol is heated to reflux for 18 hrs. The mixture is cooled and concentrated under reduced pressure to a mixture of crystals and an oil. The residual material is partitioned between water and chloroform, and the water layer subsequently separated and washed with fresh chloroform (2 × 100 ml.). All the chloroform extracts are combined, dried over sodium sulfate and concentrated in vacuo. The residue is taken up in a minimum amount of ethyl acetate from which it crystallizes on standing, 1.245 g., m.p. 174°–177° C.

h. Starting with the requisite acetophenone and 2-aminopyridine and repeating the procedure of Preparation AI-g, the following intermediate 2-Arylimidazo[1,2-a]pyridines are prepared:

2-(4-methoxyphenyl)imidazo[1,2-a]pyridine, 2-(4-bromophenyl)imidazo[1,2-a]pyridine, 2-(4-tolyl)imidazo[1,2-a]pyridine, and 2-(4-chlorophenyl)imidazo[1,2-a]pyridine.

II. Imidazo[1,5-a]pyridines a. Imidazo[1,5-a]pyridine

A mixture of 32.4 g. of 2-aminomethylpyridine and 96 ml. of 97% formic acid is heated under reflux for 3.5 hrs. The resulting solution is subjected to vacuum distillation, the desired product, 2-formamidomethylpyridine, being isolated as a yellow oil crystallizes to a solid having a melting point at about room temperature.

To 13.6 g. of 2-formamidomethylpyridine in a round-bottom flask is added 25 ml. of phosphorous oxychloride. Following the exothermic reaction, the reaction mixture is cooled to room temperature, and quenched on crushed ice. The aqueous mixture is treated with sufficient 20% aqueous sodium hydroxide solution to provide a pH of 9–10, and the liberated product extracted into chloroform (3 × 300 ml.). The extracts are combined, dried over sodium sulfate and concentrated to give imidazo[1,5-a]pyridine as a light brown oil, 14.0 g.

b. The procedure of Preparation AII-a is repeated starting with the appropriate reagents to provide the following intermediates:

1-phenylimidazo[1,5-a]pyridine and 3-phenylimidazo[1,5-a]pyridine.

III. Imidazo[1,5-a]quinolines a. Imidazo[1,5-a]quinoline

A solution of 7.7 g. of 2-cyanoquinoline in 100 ml. of acetic acid is treated with 500 mg. of 5% palladium-on-carbon, and the resulting mixture shaken in a hydrogen atmosphere at room temperature at an initial pressure of 50 psi. When the theoretical amount of hydrogen has been taken up, the catalyst is filtered and the filtrate concentrated in vacuo to a brown oil. Water is added to the residue and rendered basic by the addition of 1N aqueous sodium hydroxide. The product, 2-aminomethylquinoline, is extracted into benzene. The benzene extracts are combined, dried and concentrated to an oil, which is used without further purification.

Following the procedure of Preparation AIII-a, 7.92 g. of 2-aminomethylquinoline is formylated with 50 ml. of 97% formic acid to give 5.97 g. of 2-formamidomethylquinoline, m.p. 108°–114° C.

Treatment of 1.86 g. of 2-formamidomethylquinoline with 15 ml. of phosphorous oxychloride as in Preparation AIII-a gave imidazo[1,5-a]quinoline, which is used without purification.

IV. Imidazo[5,1-a]isoquinolines a. Imidazo[5,1-a]isoquinoline

The procedure of Zimmer, et al., Tet. Letters, #24, 2805(1968), is employed for the synthesis of this intermediate.

V. Pyrazolo[1,5-a]pyridines a. Pyrazolo[1,5-a]pyridine

The procedure of D. Dunham, Ph.D. Thesis, Ohio University, Athens, Ohio, is employed for the preparation of this intermediate.

VI. Pyrrolo[1,2-a]pyrazines a. Pyrrolo[1,2-a]pyrazine

The procedure of D. Dunham. Ph.D. Thesis, Ohio University, Athens, Ohio, is employed for the synthesis of this intermediate.

VII. Pyrrolo[1,2-a]quinoxalines a. Pyrrolo[1,2-a]quinoxaline

The procedure as taught by Cheeseman, et al., *J. Chem. Soc.*, 852 (1966) is employed for the synthesis of this intermediate.

PREPARATION B

I. Aralkyl Halides a. Benzyl halides

The benzyl halides employed as intermediates leading to the claimed compounds are commercially available, or can be prepared by processes in the chemical literature such as those taught by Wagner and Zook "Synthetic Organic Chemistry," John Wiley and Sons, New York, 1953, pp. 88–147.

b. Heterocyclic Alkyl halides

These halide intermediates are commerical materials or are synthesized by known preparatory procedures such as those taught in the aforementioned Wagner and Zook reference.

What is claimed is:

1. A compound selected from the group consisting of

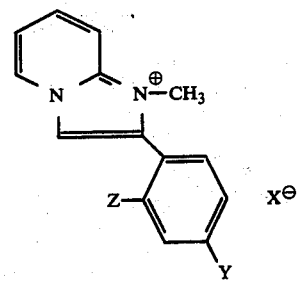

wherein Y is chlorine, bromine or methoxy; Z is hydrogen or chlorine; and X is a pharmaceutically acceptable anion.

2. The compound of claim 1, 1-methyl-2-(4-chlorophenyl)imidazo[1,2-a]pyridinium iodide.
3. The compound of claim 1, 1-methyl-2-(4-bromophenyl)imidazo[1,2-a]pyridinium iodide.
4. The compound of claim 1, 1-methyl-2-(4-methoxyphenyl)imidazo[1,2-a]pyridinium iodide.

* * * * *